United States Patent [19]

Umeno et al.

[11] Patent Number: 4,761,493

[45] Date of Patent: Aug. 2, 1988

[54] PREPARATION PROCESS OF QUATERNARY PHOSPHONIUM HYDROXIDE

[75] Inventors: Masayuki Umeno, Chigasaki; Satoshi Takita, Atsugi, both of Japan

[73] Assignee: Hokko Chemical Industry Co., Ltd., Tokyo, Japan

[21] Appl. No.: 24,074

[22] Filed: Mar. 10, 1987

[30] Foreign Application Priority Data

Mar. 12, 1986 [JP] Japan ................................. 61-52593

[51] Int. Cl.$^4$ ............................................. C07F 9/02
[52] U.S. Cl. ..................................................... 568/11
[58] Field of Search ............................................. 568/11

[56] References Cited

U.S. PATENT DOCUMENTS

| | | | |
|---|---|---|---|
| 3,299,143 | 1/1967 | Grayson et al. | 568/11 X |
| 3,364,245 | 1/1968 | Grayson et al. | 568/11 X |
| 3,452,098 | 6/1969 | Vullo | 568/11 |
| 4,189,449 | 2/1980 | Hestermann et al. | 568/11 |
| 4,260,826 | 4/1981 | Harris et al. | 568/11 |
| 4,266,079 | 5/1981 | Doorakian et al. | 568/11 |

Primary Examiner—Paul F. Shaver
Attorney, Agent, or Firm—Larson and Taylor

[57] ABSTRACT

A quaternary phosphonium hydroxide, which is represented by the following general formula (II):

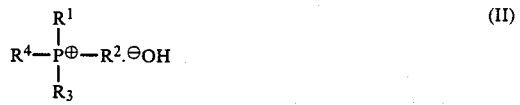

(II)

wherein $R^1$, $R^2$, $R^3$ and $R^4$ mean independently an alkyl group having 1-8 carbon atoms, a phenyl group or a benzyl group, is prepared by dissolving a quaternary phosphonium halide represented by the following general formula (I):

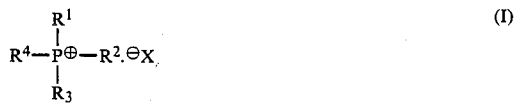

(I)

wherein $R^1$, $R^2$, $R^3$ and $R^4$ has the same meaning as defined above and X denotes a chlorine, bromine or iodine atom, in a solvent selected from water, lower alcohols and aqueous lower alcohols, and then bringing the resultant solution into contact with a strongly basic anion exchange resin (OH-form).

9 Claims, No Drawings

PREPARATION PROCESS OF QUATERNARY PHOSPHONIUM HYDROXIDE

SUMMARY OF THE INVENTION

This invention relates to a process for the preparation of a quaternary phosphonium hydroxide. The quaternary ammonium hydroxide of the general formula (II) given below is useful as a polymerization catalyst for use in the production of a polysiloxane as shown by the following reaction equation (A):

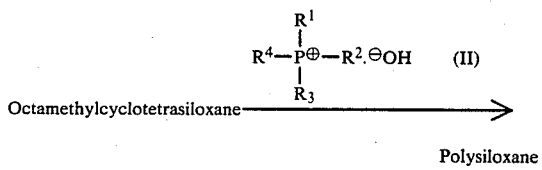

In the general formula (II), $R^1$, $R^2$, $R^3$ and $R^4$ mean independently an alkyl group having 1-8 carbon atoms, a phenyl group or a benzyl group.

BACKGROUND OF THE INVENTION

Polysiloxane-forming reactions of the above sort are disclosed, for example, in the "J. Polymer Sci." 54, 375 (1961) and U.K. Patent Specification No. 794,119.

For the preparation of quaternary phosphonium hydroxides, it has been known to react tetra-n-butylphosphonium iodide with silver oxide in an aqueous medium as shown by the following reaction formula (B) (see, U.K. Patent Specification No. 794,119 and U.S. Pat. No. 2,883,366).

$$(n\text{-}Bu)_4PI + \tfrac{1}{2}Ag_2O + \tfrac{1}{2}H_2O \rightarrow (n\text{-}Bu)_4POH + AgI \quad (B)$$

wherein n-Bu means a n-butyl group.

The above-described conventional process making use of silver oxide resulted in a very high production cost due to the high price of the silver oxide reagent and was hence not a satisfactory synthetic process from the industrial viewpoint. In addition, the reaction of the above conventional process was not a practical reaction in view of its low reactivity except for the use of the iodide as the halide, because the reaction velocity is extremely slow when the bromide or chloride is used as the halide.

DETAILED DESCRIPTION OF THE INVENTION

With the foregoing in view, the present invention has a principal object to provide an easy and economical process for the preparation of a quaternary phosphonium hydroxide represented by the general formula (II).

In one aspect of this invention, there is thus provided a procss for the preparation of a quaternary phosphonium hydroxide represented by the following general formula (II):

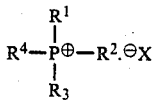

wherein $R^1$, $R^2$, $R^3$ and $R^4$ mean independently an alkyl group having 1-8 carbon atoms, a phenyl group or a benzyl group, which comprises dissolving a quaternary phosphonium halide represented by the following general formula (I):

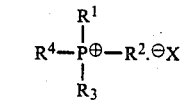

wherein $R^1$, $R^2$, $R^3$ and $R^4$ has the same meaning as defined above and X denotes a chlorine, bromine or iodine atom, in a solvent selected from water, lower alcohols and aqueous lower alcohols, and then bringing the resultant solution into contact with a strongly basic anion exchange resin (OH-form), to exchange the halide anion (X) of the compound of formula (I) by the hydroxyl anion (OH) of the anion exchange resin.

The process of this invention can easily prepare the quaternary phosphonium hydroxide (II) in the form of a solution at an extremely low cost.

The above and other objects, features and advantages of the present invention will become apparent from the following description of the invention and the appended claims.

PREFERRED EMBODIMENTS OF THE INVENTION

The process of this invention may be conducted, for example, in the following manner. First of all, there is provided a column packed with a strongly basic anion exchange resin (OH-form), particularly a synthetic polymer containing quaternary tri-alkyl ammonium hydroxide groups as the anion exchange functions, for example, "Amberlite IRA-400" (OH-form) (a trade name of a product of Rhom & Haas Co., U.S.A.; comprising styrene polymer containing quaternary ammonium chloride or hydroxide groups as the function groups) or "Amberlyst A-26" (OH-form) (a styrene copolymer containing quaternary ammonium hydroxide groups). A solution of a quaternary phosphonium halide of the formula (I) as a starting material is then passed into the column. The column is then eluted with an eluent so that a solution of the resultant quaternary phosphonium hydroxide of the formula (II) is obtained as an eluate. As the solvent, water, a lower alcohol such as a ($C_1$–$C_4$)-alcohol, for example, methanol, ethanol, n-propanol, isopropanol, n-butanol and iso-butanol, a water-containing or aqueous lower alcohol or the like may be used. It is important that the solvent is used in a deionized form. Although no particular limitation is imposed on the concentration of the starting material in the solution, the concentration may preferably be from 10% to 40% (by weight) for easy operation of the process. The rate of elution may range from 0.1 to 50 ml/cm²/min., with 1–10 ml/cm²/min. being preferred. The temperature of operating the process may range from 0° C. to 60° C., with 10°–50° C. being preferred.

The quaternary phosphonium halide which is remaining unreacted is also eluted out into the eluate of the quaternary phosphonium hydroxide of the formula (II) coming from the column. When water is used as a solvent, the unreacted quaternary phosphonium halide can be removed by extracting the aqueous eluate with a halogenated hydrocarbon solvent such as dichloromethane or chloroform, so that the quaternary phosphonium hydroxide (II) may be obtained in its highly pure state in the form of an aqueous solution.

The present invention has brought about numerous advantages.

First of all, the preparation cost of the quaternary phosphonium hydroxide (II) was high in the conventional processes because costly silver oxide was used. According to the present invention, the intended quaternary phosphonium hydroxide (II) can very much inexpensively be obtained as a pure solution thereof.

Secondly, the iodide ion was only effective as the halide ion which may be present in the starting material, i.e., the quaternary phosphonium halide (I) when the conventional processes were resorted on. According to the present invention, the chloride, bromide and iodide ions may all be effective to be present in the starting compound (II). The process of this invention can thus be applied to a broader range of quaternary phosphonium halides (I). In view of the fact that an iodide compound is generally more expensive than its corresponding bromide and chloride compounds, the present invention can also contribute to the reduction in the preparation cost of the intended quaternary phosphonium hydroxide solution.

Thirdly, the intended quaternary phosphonium hydroxide (II) can be produced in a high yield and in a simple manner by causing a solution of the starting material, i.e., the corresponding quaternary phosphonium halide to pass through a column of the anion exchange resin.

The process of this invention will next be described specifically by the following Examples.

EXAMPLE 1

A column having an inner diameter of 25 mm was packed with 150 ml of "Amberlite IRA-400" (Cl-form; trade name, as sold from Japan Organo Co., Ltd.) which had been allowed to swell fully in water.

Thereafter, 390 g (975 mmoles) of a 10% solution of sodium hydroxide in water was caused to pass at a flow rate of 4 ml/cm$^2$/min. through the column, thereby converting the resin into the OH-form. Using deionized water, the resin was then washed until the aqueous washings became neutral.

In 112 ml of deionized water was dissolved 28.0 (82.5 mmoles) of tetra-n-butylphosphonium bromide. The solution obtained was charged into the above-prepared resin column and the column was thereafter eluted with deionized water. The major fractions of the eluate (totally, about 180 ml) containing a large amount of the intended compound, tetra-n-butylphosphonium hydroxide were collected.

The combined aqueous solution of the collected principal fractions was extracted twice with 180 ml of dichloromethane so as to extract out the unreacted tetra-n-butylphosphonium bromide. By distilling off at reduced pressure the dichloromethane which still remained in a trace amount in the aqueous solution thus extracted, 180 ml of an aqueous solution of highly pure tetra-n-butylphosphonium hydroxide was obtained (the concentration: 0.375 mole/l, yield: 81.8%).

The unreacted tetra-n-butylphosphonium bromide remaining in the aqueous solution so obtained was in a trace amount. Incidentally, 3.3 g of the unreacted tetra-n-butylphosphonium bromide was recovered from the dichloromethane extract (recovery yield: 11.8%).

EXAMPLE 2

Following the procedure of Example 1, there was prepared a column having an inner diameter of 15 mm and packed with 50 ml of "Amberlite IRA-400" (OH-form).

In 7.7 ml of deionized water, was dissolved 7.9 g (26.8 mmoles) of tetra-n-butylphosphonium chloride. Similarly to Example 1, the solution was caused to pass through the column, followed by elution of the column with deionized water so that the major principal fractions of the eluate (totally 50 ml) containing a large amount of the intended compound, tetra-n-butylphosphonium hydroxide were collected (the concentration: 0.375 mole/l, yield: 70.2%).

Incidentally, 1.2 g of the unreacted tetra-n-butylphosphonium chloride was remaining in the aqueous eluate thus obtained.

EXAMPLE 3

Following the procedure of Example 1, there was prepared a column having an inner diameter of 15 mm and packed with 50 ml of "Amberlyst A-26" (OH-form). A 1:1 (by volume) mixed solvent of deionized water and methanol was then caused to pass through the column so that the mixed solvent substituted for the solvent which had been present in the anion exchange resin employed.

In 20.9 ml of the 1:1 (by volume) mixed solvent of deionized water and methanol was dissolved 10.6 g (27.5 mmoles) of tetra-n-butylphosphonium iodide. Similarly to Example 1, the resultant solution was caused to pass through the above column, followed by elution with the 1:1 (by volume) mixed solvent of deionized water and methanol so that the major fractions of the eluate (totally 60 ml) containing the intended compound, tetra-n-butylphosphonium hydroxide, in a large amount was collected (concentration: 0.380 mole/l, yield: 82.9%).

Incidentally, 1.3 g of the unreacted tetra-n-butylphosphonium iodide was remaining in the eluate thus obtained.

EXAMPLE 4

Following the procedure of Example 1, there was prepared a column having an inner diameter of 15 mm and packed with 50 ml of "Amberlyst A-26" (OH-form). Methanol was then caused to pass through the column so that the methanol substituted for the solvent which had been present in the anion exchange resin employed.

In 20 ml of methanol was dissolved 26.2 g (14.1 mmoles) of tetra-n-octylphosphonium bromide. Similarly to Example 1, the resultant solution was caused to pass through the above column, followed by elution with methanol so that the major principal fractions of the eluate (64 ml) containing a large amount of the intended compound, tetra-n-octylphosphonium hydroxide were collected together (the concentration: 0.20 mole/l, yield: 90.8%).

Incidentally, 0.7 g of the unreacted tetra-n-octylphosphonium bromide was remaining in the aqueous eluate obtained.

EXAMPLE 5

Following the procedure of Example 1, there was prepared a column having an inner diameter of 15 mm and packed with 50 ml of "Amberlyst A-26" (OH-form). Methanol was then caused to pass through the column so that the methanol substituted for the solvent which had been present in the anion exchange resin.

In 17 ml of methanol, 11.5 g (27.5 mmoles) of tetra-phenylphosphonium bromide was dissolved. Similarly to Example 1, the resultant solution was caused to pass through the above column, followed by elution with methanol so that the major fractions of the eluate (63 ml) containing a large amount of the intended compound, tetra-phenylphosphonium hydroxide were collected together (the concentration: 0.29 mole/l, yield: 66.4%).

Incidentally, 3.0 g of the unreacted tetra-phenylphosphonium bromide was remaining in the eluate obtained.

EXAMPLE 6

Following the procedure of Example 1, there was prepared a column having an inner diameter of 15 mm and packed with 50 ml of "Amberlyst A-26" (OH-form). A 1:1 (by volume) mixed solvent of deionized water and methanol was then caused to pass through the column so that the 1:1 (by volume) mixed solvent of deionized water and methanol substituted for the solvent which had been contained in the anion exchange resin.

In 18.2 ml of the 1:1 (by volume) mixed solvent of deionized water and methanol, 10.4 g (27.5 mmoles) of di-n-butyl-diphenylphosphonium bromide was dissolved. Similarly to Example 1, the resultant solution was caused to pass through the above column, followed by elution with the 1:1 (by volume) mixed solvent of deionized water and methanol so that the major fractions of the eluate (totally 66 ml) containing a large amount of the intended compound, di-n-butyl-diphenyl-phosphonium hydroxide were collected (the concentration: 0.286 mole/l, yield: 68.6%).

Incidentally, 2.6 g of the unreacted di-n-butyl-diphenylphosphonium bromide was present in the eluate solution.

EXAMPLE 7

Following the procedure of Example 1, there was prepared a column having an inner diameter of 15 mm and packed with 50 ml of "Amberlyst A-26" (OH-form).

In 18 ml of deionized water and methanol, 9.05 g (27.5 mmoles) of benzyl-tri-n-butylphosphonium chloride was dissolved. Similarly to Example 1, the resultant solution was caused to pass through the above column, followed by elution with deionized water so that the major fraction of the eluate (102 ml) containing a large amount of the intended compound, benzyl-tri-n-butyl-phosphonium hydroxide were collected together (the concentration: 0.206 mole/l, yield: 76.4%).

Incidentally, 0.9 g of the unreacted benzyl-tri-n-butylphosphonium chloride was co-existing in the eluate thus obtained.

Having now fully described the invention, it will be apparent to one of ordinary skill in the art that many changes and modifications can be made thereto without departing from the spirit or scope of the invention as set forth herein.

What is claimed is:

1. A process for the preparation of a quaternary phosphonium hydroxide represented by the following general formula (II):

wherein $R^1$, $R^2$, $R^3$ and $R^4$ mean independently an alkyl group having 1–8 carbon atoms, a phenyl group or a benzyl group, which comprises dissolving a quaternary phosphonium halide represented by the following general formula (I):

wherein $R^1$, $R^2$, $R^3$ and $R^4$ has the same meaning as defined above and X denotes a chlorine, bromine or iodine atom, in a solvent selected from water, lower alcohols and aqueous lower alcohols, and then bringing the resultant solution into contact with a strongly basic anion exchange resin (OH-type).

2. The process as claimed in claim 1, wherein the strongly basic anion exchange resin (OH-form) is packed in a column.

3. The process as claimed in claim 2, wherein the quaternary phosphonium halide (I) is dissolved in a solvent to a concentration of 10–40%.

4. The process as claimed in claim 2, wherein the column is eluted with an eluent at a rate of 0.1–50 ml/cm$^2$/min. and at 0°–60° C.

5. The process as claimed in claim 2, wherein the solvent is de-ionized water, methanol or a mixture thereof and the same solvent is used as an eluent to elute the column.

6. The process as claimed in claim 5, wherein the solvent and eluent are both de-ionized water, and the process further comprises extracting the resultant eluate with a halogenated hydrocarbon solvent to form an aqueous solution of the quaternary phosphonium hydroxide (II) in a highly pure form.

7. The process as claimed in claim 6, wherein the halogenated hydrocarbon solvent is dichloromethane or chloroform.

8. The process as claimed in claim 1, wherein the strongly basic anion exchange resin is Amberlite IRA-400 (OH-form) or Amberlyst A-26 (OH-form).

9. The process as claimed in claim 1, wherein the quaternary phosphonium halide (I) is tetra-n-butylphosphonium bromide, tetra-n-butylphosphonium chloride, tetra-n-butylphosphonium iodide, tetra-n-octylphosphonium bromide, tetra-phenylphosphonium bromide, di-n-butyl-diphenylphosphonium bromide or benzyl-tri-n-butylphosphonium bromide.

* * * * *